United States Patent
George et al.

(10) Patent No.: US 11,045,176 B2
(45) Date of Patent: Jun. 29, 2021

(54) SPECIMEN RETRIEVAL DEVICE

(71) Applicant: Covidien LP, Mansfield, MA (US)

(72) Inventors: Sabastian Koduthully George, Hyderabad (IN); Raja Kamaraj, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 216 days.

(21) Appl. No.: 16/299,184

(22) Filed: Mar. 12, 2019

(65) Prior Publication Data

US 2019/0350570 A1 Nov. 21, 2019

Related U.S. Application Data

(60) Provisional application No. 62/673,176, filed on May 18, 2018.

(51) Int. Cl.
*A61B 17/221* (2006.01)
*A61B 17/00* (2006.01)

(52) U.S. Cl.
CPC ........... *A61B 17/00234* (2013.01); *A61B 2017/00287* (2013.01); *A61B 2017/00367* (2013.01); *A61B 2017/00862* (2013.01)

(58) Field of Classification Search
CPC . A61B 17/00; A61B 17/221; A61B 17/00234; A61B 2017/00862; A61B 2017/00367; A61B 2017/00287
See application file for complete search history.

(56) References Cited

U.S. PATENT DOCUMENTS

| | | |
|---|---|---|
| 30,471 A | 10/1860 | Dudley |
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |

(Continued)

FOREIGN PATENT DOCUMENTS

| | | |
|---|---|---|
| DE | 3542667 A1 | 6/1986 |
| DE | 8435489 U1 | 8/1986 |

(Continued)

OTHER PUBLICATIONS

European Search Report EP 12191639.9 dated Feb. 20, 2013.

(Continued)

*Primary Examiner* — Vi X Nguyen

(57) ABSTRACT

A specimen retrieval device includes a tubular body defining a longitudinal bore, an inner shaft slidably disposed within the longitudinal bore of the tubular body, and a specimen bag affixed to a support mechanism at the distal portion of the inner shaft. The specimen retrieval device includes a drain tube that passes from within specimen bags and out of the specimen retrieval device that permits passage of fluids out of the specimen bag prior to removal of the device from the body.

12 Claims, 5 Drawing Sheets

(56) References Cited

U.S. PATENT DOCUMENTS

| | | |
|---|---|---|
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |

(56) References Cited

U.S. PATENT DOCUMENTS

| | | | |
|---|---|---|---|
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073745 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1* | 6/2007 | Hart ................. A61B 17/00234 604/327 |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2017/0049427 A1 | 2/2017 | Do et al. |
| 2017/0215904 A1* | 8/2017 | Wassef ............. A61B 17/32002 |
| 2017/0224321 A1 | 8/2017 | Kessler et al. |
| 2017/0311964 A1 | 11/2017 | Desai et al. |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| ES | 2379920 A1 | 5/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2014134285 A1 | 9/2014 |
| WO | 2015134888 A1 | 9/2015 |
| WO | 2017189442 A1 | 11/2017 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.

(56) References Cited

OTHER PUBLICATIONS

Extended European Search Report issued in Appl. No. 19174966.2 dated Oct. 30, 2019 (10 pages).

* cited by examiner

SPECIMEN RETRIEVAL DEVICE

CROSS-REFERENCE TO RELATED APPLICATION

This application claims the benefit of and priority to U.S. Provisional Patent Application No. 62/673,176 filed May 18, 2018, the entire disclosure of which is incorporated by reference herein.

TECHNICAL FIELD

The present disclosure relates generally to surgical apparatuses for use in minimally invasive surgical procedures, such as endoscopic and/or laparoscopic procedures and, more particularly, the present disclosure relates to specimen retrieval devices including an opening that may be closed after placement of a tissue specimen therein.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit visual inspection and magnification of a body cavity. The surgeon can then perform diagnostic and/or therapeutic procedures at the surgical site with the aid of specialized instrumentation, such as forceps, graspers, cutters, applicators, and the like, which are designed to fit through additional cannulas.

When removing certain tissues from the body cavity, for example tumor tissue, it is important that the tumor tissue does not come into contact with healthy or uninvolved tissue. If tumor tissue or tissue parts have to be removed, they may be introduced into an "extraction bag," also referred to herein as a "specimen bag," at the site where the tumor or diseased tissue has been detached from the surrounding tissue, after which the specimen bag is withdrawn from the body, thereby minimizing contact of the diseased tissue with healthy tissue.

Improved specimen bags for use in minimally invasive surgical procedures remain desirable.

SUMMARY

Specimen retrieval devices in accordance with the present disclosure include a pouch having a drain tube therein. In embodiments, a specimen retrieval device of the present disclosure includes a tubular body defining a longitudinal bore, the tubular body having a proximal portion, a distal portion, and a hand grip supported on the proximal portion of the tubular body; an inner shaft having a proximal portion, a distal portion, an actuation handle supported on the proximal portion of the inner shaft, and a support member extending from a distal portion of the inner shaft; a specimen bag supported on the support member at the distal portion of the inner shaft, the specimen bag including a body defining an opening; and a drain tube defining a longitudinal bore, the drain tube having a proximal portion, a distal portion within the opening of the body of the specimen bag, and pores at the distal portion of the drain tube.

In embodiments, the support member includes a pair of resilient fingers which support the specimen bag and open the opening of the specimen bag in a deployed state.

In some embodiments, the resilient fingers are positioned adjacent the opening of the specimen bag.

In embodiments, the specimen bag is furled about the inner shaft in a non-deployed state.

In other embodiments, the specimen retrieval device also includes at least one pull string having a proximal portion and a distal portion encompassing the opening of the specimen bag, wherein the proximal portion of the pull string extends proximally from the actuation handle.

In some embodiments, the at least one pull string includes two pull strings.

In other embodiments, the proximal portion of each of the two pull strings extends proximally from the actuation handle.

In embodiments, the drain tube passes through the longitudinal bore of the tubular body.

In some embodiments, the proximal portion of the drain tube extends from the proximal portion of the tubular body.

Methods using the specimen retrieval devices of the present disclosure are also provided. In embodiments, a method of the present disclosure includes introducing a tubular body of a specimen retrieval device through a body opening into a body cavity; introducing an inner shaft having a proximal portion and a distal portion through a longitudinal bore of the tubular body; moving an inner shaft including a support member within a longitudinal bore of the tubular body to position a specimen bag supported on the support member within the body cavity; passing a tissue specimen through an opening of the specimen bag into the specimen bag; removing fluids within the body of the specimen bag through a drain tube and out of the specimen bag; and removing the specimen retrieval device from the body cavity.

In embodiments, methods of the present disclosure further include breaking up the tissue specimen in the specimen bag prior to removing the specimen retrieval device from the body cavity.

In some embodiments, methods of the present disclosure further include applying a vacuum source to a proximal portion of the drain tube to draw the fluids out of the specimen bag.

In other embodiments, methods of the present disclosure further include closing the opening of the specimen bag after removing the fluids from the specimen bag.

In embodiments, closing the opening of the specimen bag occurs before removing the specimen retrieval device from the body cavity.

In some embodiments, closing the opening of the specimen bag occurs by proximally pulling a pull string extending about the opening of the specimen bag.

BRIEF DESCRIPTION OF THE DRAWINGS

Embodiments of the presently disclosed specimen retrieval device are described hereinbelow with reference to the drawings wherein.

DETAILED DESCRIPTION OF THE EMBODIMENTS

Figure 1:
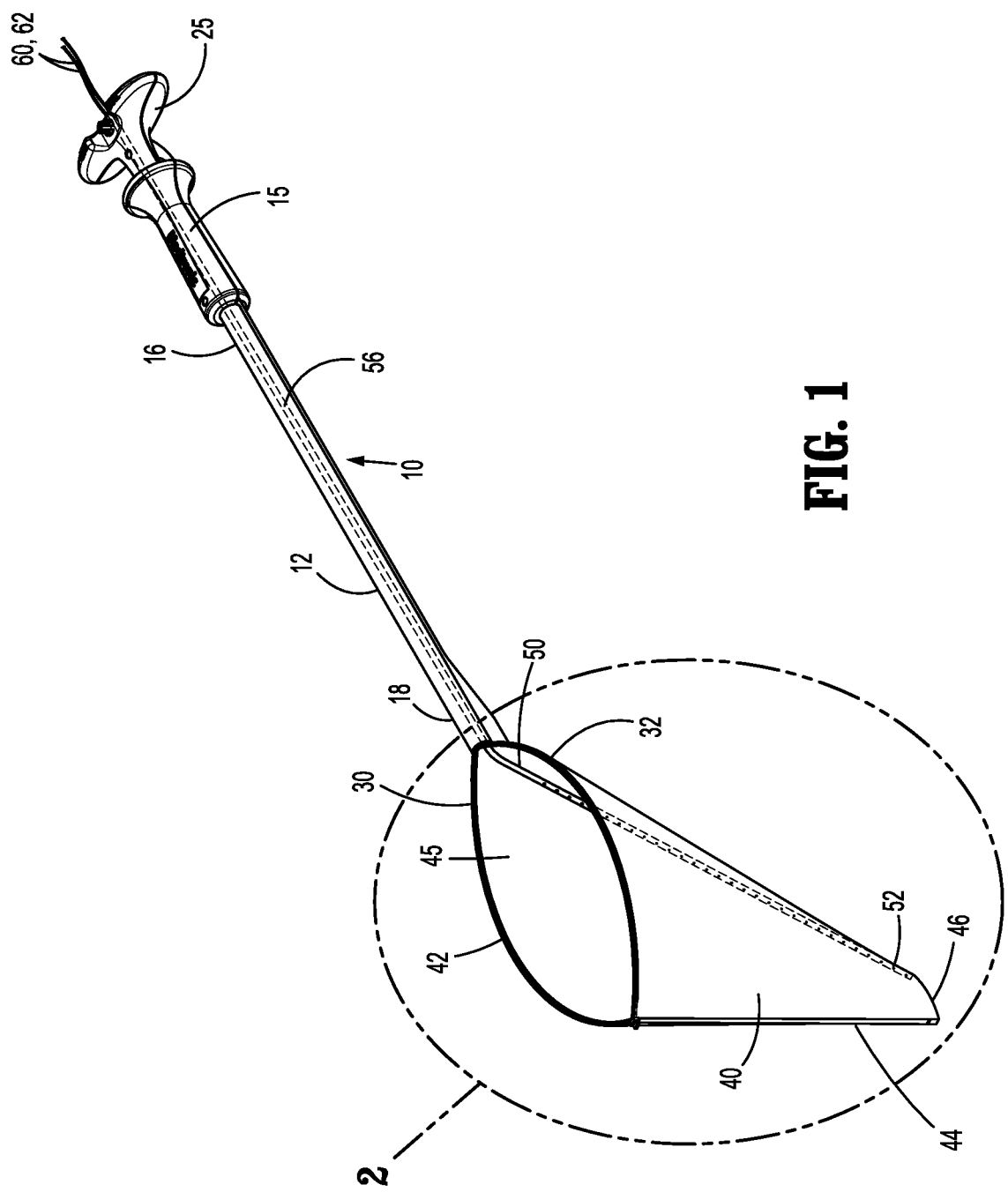
FIG. 1 is a side perspective view of a specimen retrieval device in accordance with an exemplary embodiment of the present disclosure with a specimen bag deployed.

The present disclosure provides a specimen retrieval device for use in minimally invasive surgical procedures. As used herein with reference to the present disclosure, minimally invasive surgical procedures encompass laparoscopic procedures, arthroscopic procedures, and endoscopic procedures, and refer to procedures utilizing scopes or similar devices having relatively narrow operating portions capable of insertion through a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

The presently disclosed specimen retrieval device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. The term "clinician" is used generally to refer to medical personnel including doctors, surgeons, nurses, and support personnel.

Figure 2:
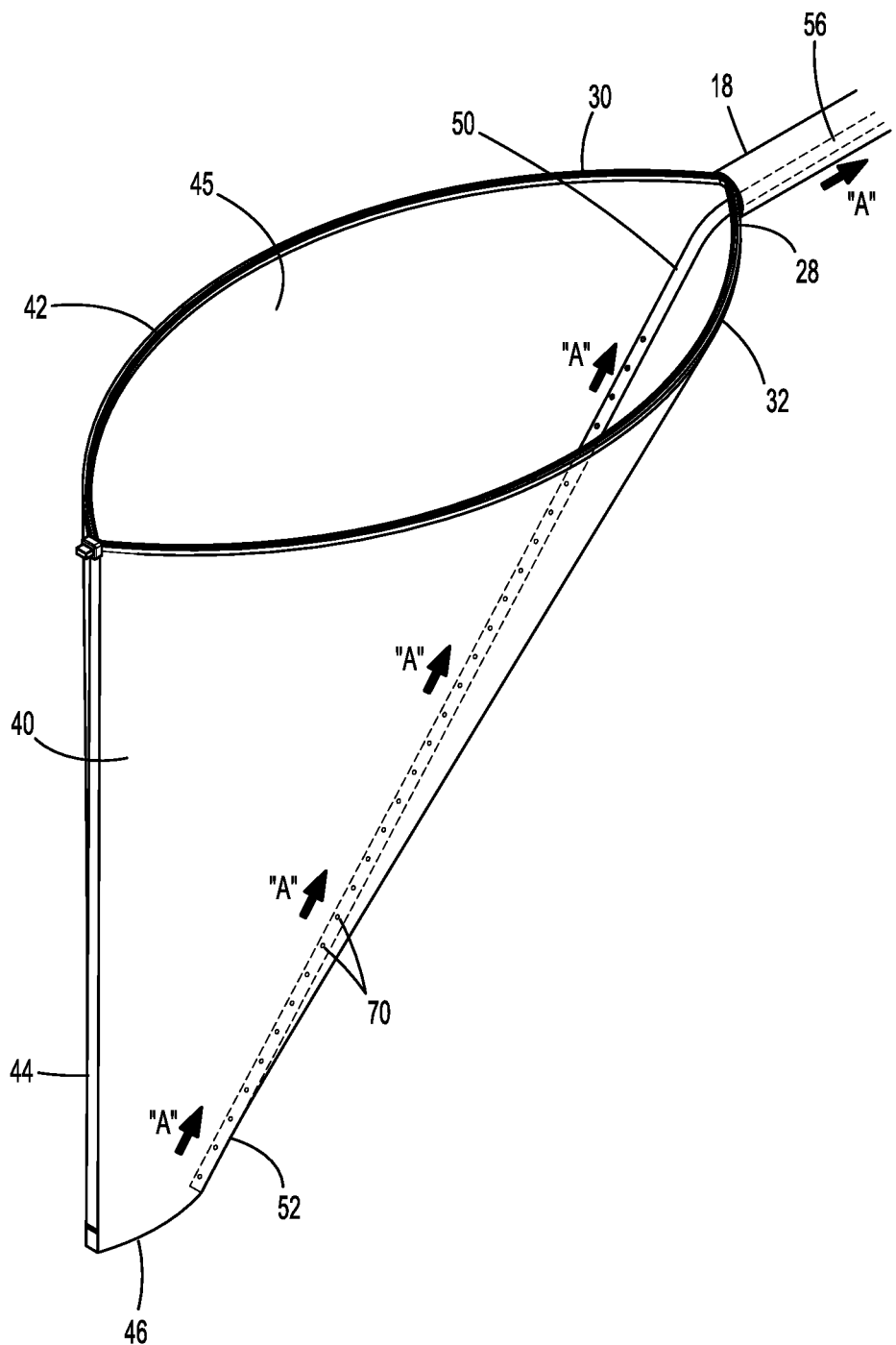
FIG. 2 is an enlarged view of the indicated area of detail shown in FIG. 1.
Figure 3:
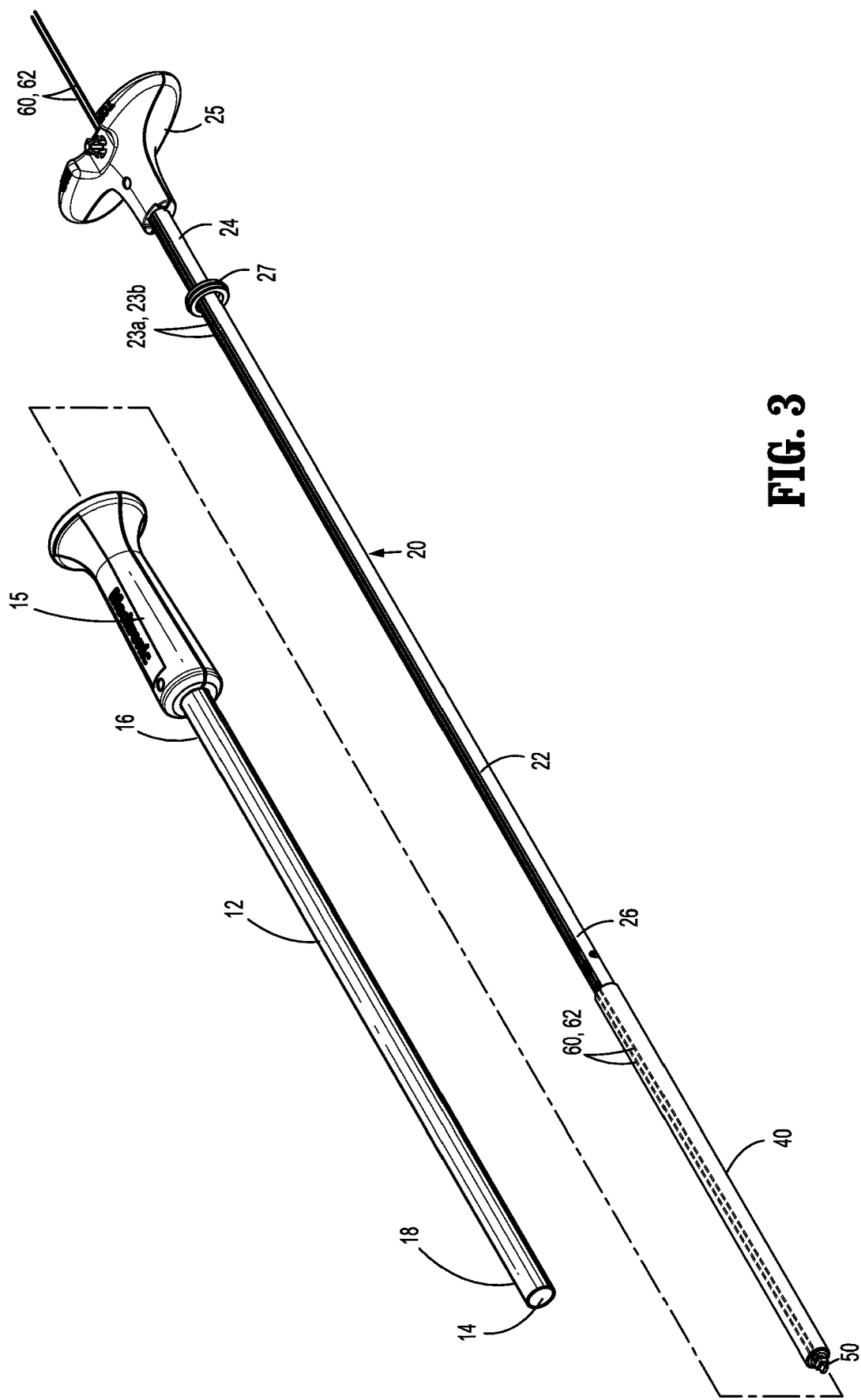
FIG. 3 is a side perspective view showing the specimen retrieval device shown in FIG. 1 with a tubular body separated from an inner shaft assembly and the specimen bag furled about the inner shaft assembly.

Referring to FIGS. 1-5, and initially with reference to FIGS. 1-3, the specimen retrieval device 10 of the present disclosure includes a tubular body 12 having a proximal portion 16 and a distal portion 18, and defines a longitudinal bore 14 that extends between the proximal portion 16 and the distal portion 18. The tubular body 12 has a hand grip 15 thereon. The specimen retrieval device 10 also includes an inner shaft assembly 20 (FIG. 3) including an inner shaft 22 slidably positioned within the longitudinal bore 14 of the tubular body 12, an actuation handle 25 secured to a proximal portion 24 of the inner shaft 22, and a specimen bag 40 (FIG. 1) supported on a distal portion 26 of the inner shaft 22.

The hand grip 15 on the tubular body 12 may be formed as a unitary component or, as depicted in FIG. 6, as two separate half components 15a, 15b, that are coupled to one another about the tubular body 12 by one or more suitable coupling methods (e.g., one or more suitable adhesives). In the latter instance, as shown in FIG. 6, an indent/detent configuration may be utilized to facilitate coupling the two separate half components on 15a, 15b to one another.

The actuation handle 25 on the inner shaft 22 may likewise be formed as a unitary component or, in embodiments, as depicted in FIG. 6, as two separate half components 25a, 25b that are coupled to one another by one or more suitable coupling methods (e.g., one or more suitable adhesives). An O-ring 27 (FIG. 3) may be secured to the proximal portion 24 of the inner shaft 22. The O-ring 27 is configured to provide a fluid tight seal between the longitudinal bore 14 and the inner shaft 22 while allowing substantially unhindered translation of the inner shaft 22 with respect to the tubular body 12 when the inner shaft 22 is translated in the proximal and/or distal directions. The fluid tight seal prevents insufflation gases in a working space, e.g., within a body cavity of a patient, from escaping through the longitudinal bore 14 of the tubular body 12.

In an assembled configuration, the hand grip 15 and the actuation handle 25 can be manipulated to facilitate manipulation of the specimen retrieval device 10 and the sliding of the inner shaft 22 within the tubular body 12. More specifically, the hand grip 15 can be grasped by the clinician with one hand and the actuation handle 25 can be grasped by the clinician with the other hand to move the inner shaft 22 within the tubular body 12 to deploy the specimen bag 40 from within the tubular body 12.

The tubular body 12 and/or the inner shaft assembly 22 of the present disclosure are made of biocompatible materials within the purview of those skilled in the art, in embodiments, polymeric materials. For example, the tubular body 12 and/or the inner shaft assembly 22 may be made of thermoplastic polyurethanes sold under the name PELLETHANE®, which offer flexibility and a wide range of hardness. The tubular body 12 and/or the inner shaft assembly 22, for example, may be fabricated from PELLETHANE® 2363-80A, PELLETHANE® 2363-90A, PELLETHANE® 2363-55D, any combination thereof, or any alternatives within the purview of those skilled in the art.

In some embodiments, the tubular body 12 and the inner shaft assembly 22 are formed of the same material. In other embodiments, the tubular body 12 and the inner shaft assembly 22 are formed of different materials.

As depicted in FIG. 1, the specimen bag 40 includes a body 44 having a generally tubular or elongated configuration that is defined by an openable and closable portion (or mouth) 42 and a closed portion 46. The mouth 42 defines an opening 45. Alternatively, other specimen bag configurations are envisioned. Referring to FIG. 2, the distal portion 26 (FIG. 3) of the inner shaft 22 is coupled to a support member 28 that is configured to support the specimen bag 40. In embodiments, the support member 28 includes a pair of resilient fingers 30, 32 that extend distally from the distal portion 26 of the inner shaft 22. In embodiments, the resilient fingers 30, 32 can be integrally formed with the distal portion 26 of the inner shaft 22 such as by molding.

The resilient fingers 30, 32 are movable from a spaced non-deformed state (FIG. 1) to a deformed state (FIG. 3) to facilitate placement of the specimen bag 40 into the tubular body 12. The resilient fingers 30, 32 return to the non-deformed state when the specimen bag 40 is deployed from the tubular body 12 to open the mouth 42 of the specimen bag 40, as described below. Alternately, the specimen bag 40 can be supported on the distal portion 26 of the inner shaft 22 using other fastening or securing techniques.

The body 44 of the specimen bag 40 may be made from any suitable biocompatible material (e.g., nylon, urethane, ripstop nylon or latex) capable of forming a flexible collapsible member, or membrane. In embodiments, the material from which the specimen bag 40 is made is resilient, antistatic, pyrogen-free, non-toxic, and sterilizable. In embodiments, materials used to form the tubular body 12 and/or the inner shaft 22 described above may be used to form the specimen bag 40. In other embodiments, the specimen bag 40 is formed of materials that are different from those used to form the tubular body 12 and/or the inner shaft 22. The specimen bag 40 may be opaque or clear.

In embodiments, the mouth 42 of the specimen bag 40 has pull strings 60, 62 (FIG. 3) attached thereto, as well as resilient fingers 30, 32 attached thereto. In other embodiments, the resilient fingers 30, 32 and the pull strings 60, 62 may be received in a cuff (not shown) formed at the mouth 42 of the specimen bag 40. The cuff may be formed on the specimen bag 40 by any suitable method. In embodiments, for example, a top portion of the specimen bag 40 may be folded into an interior thereof or onto an exterior thereof (not shown) and, subsequently, glued thereto to form the cuff.

Referring to FIG. 3, the inner shaft 22 includes two channels 23a, 23b allowing for passage of the pull strings 60, 62, or similar devices through or along the inner shaft 22. The pull strings 60, 62 encompass the mouth 42 of the specimen bag 40. The pull strings 60, 62 pass from the mouth 42 of the specimen bag 40 through the channels 23a, 23b on the inner shaft 22 and pass through the actuation handle 25 that remains outside the tubular body 12. In alternate embodiments, a single pull string (not shown) may pass through a single channel (not shown) of the inner shaft 22 and encompass the mouth 42 of the specimen bag 40.

In use, pulling the pull strings 60, 62 proximally closes the mouth 42 of the specimen bag 40 to retain a tissue specimen (not shown) therein. However, as a practical matter, the mouth 42 may not be completely closed (not shown), with a small opening remaining at the mouth 42 of the specimen bag 40. Any opening increases chances for leakage of fluids from the specimen bag 40, which could result in complications, such as the possibility of spreading malignancy where the tissue specimen is cancerous.

Thus, to avoid the potential spilling of any fluid contents from the specimen bag 40, as depicted in FIGS. 1, 2 and 4-5, the specimen retrieval device 10 also includes a drain tube 50 which passes from the interior of the specimen bag 40 through the longitudinal bore 14 of the tubular body 12 and out of the specimen retrieval device 10. The drain tube 50 has a distal portion 52 positioned within the specimen bag 40, a proximal portion 54 extending from the actuation handle 25 attached to the inner shaft 22, and a body 56 therebetween which, as noted above, passes through the tubular body 12 of the specimen retrieval device 10. The drain tube 50 also possesses perforations, sometimes referred to herein as pores 70, at the distal portion 52 of the drain tube 50, which permit drainage of body fluids contained within the specimen bag 40.

Figure 4:
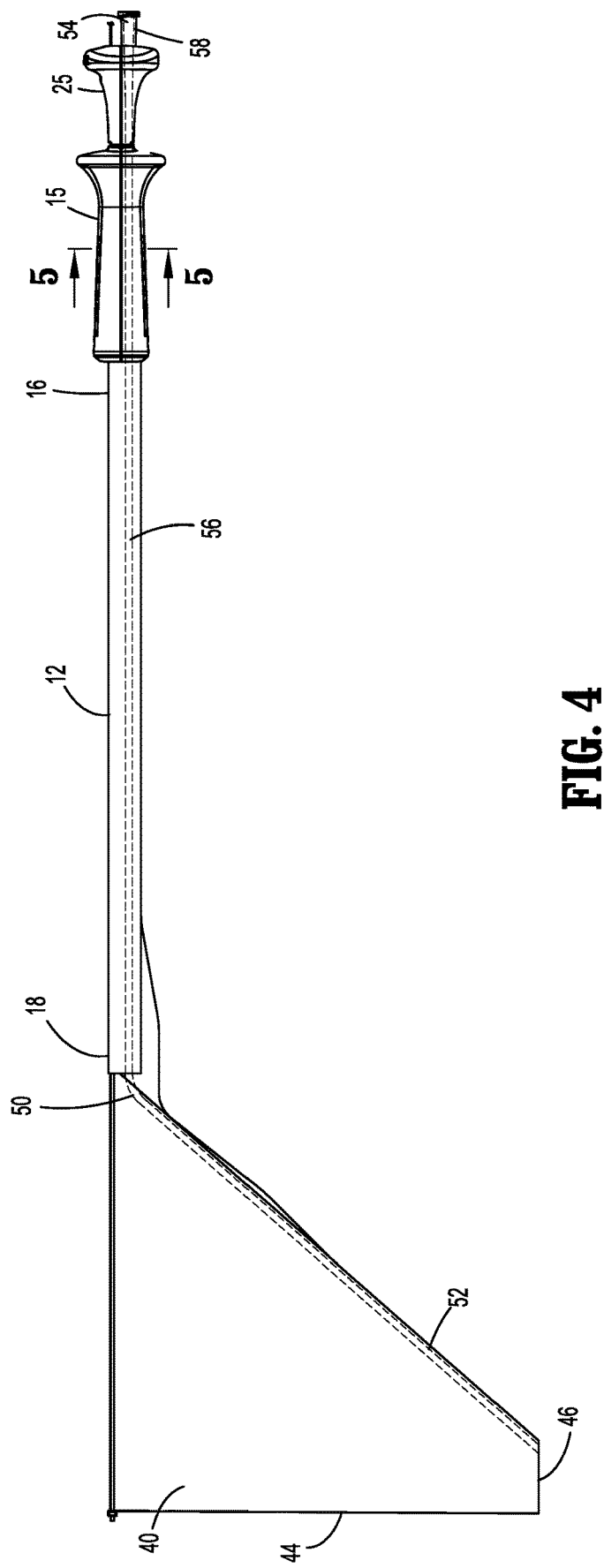
FIG. 4 is a side view of the specimen retrieval device shown in FIG. 1.

As depicted in FIGS. 2 and 4, in embodiments the distal portion 52 of the drain tube 50 is affixed to an inner wall of the body 44 of the specimen bag 40 such that the pores 70 on the distal portion 52 of the drain tube 50 are open to the interior of the specimen bag 40 and capable of drawing fluids within the specimen bag 40 through the pores 70 and into the drain tube 50.

The proximal portion 54 of the drain tube 50 may possess a luer fitting 58 (FIG. 4) or be similarly configured to permit attachment of a vacuum source (not shown) to the drain tube 50 to assist in drawing any fluids from within the specimen bag 40, through the drain tube 50, and out of the specimen retrieval device 10. The drawing of fluids through the drain tube 50 is indicated by arrows "A" in FIG. 2.

Figure 5:
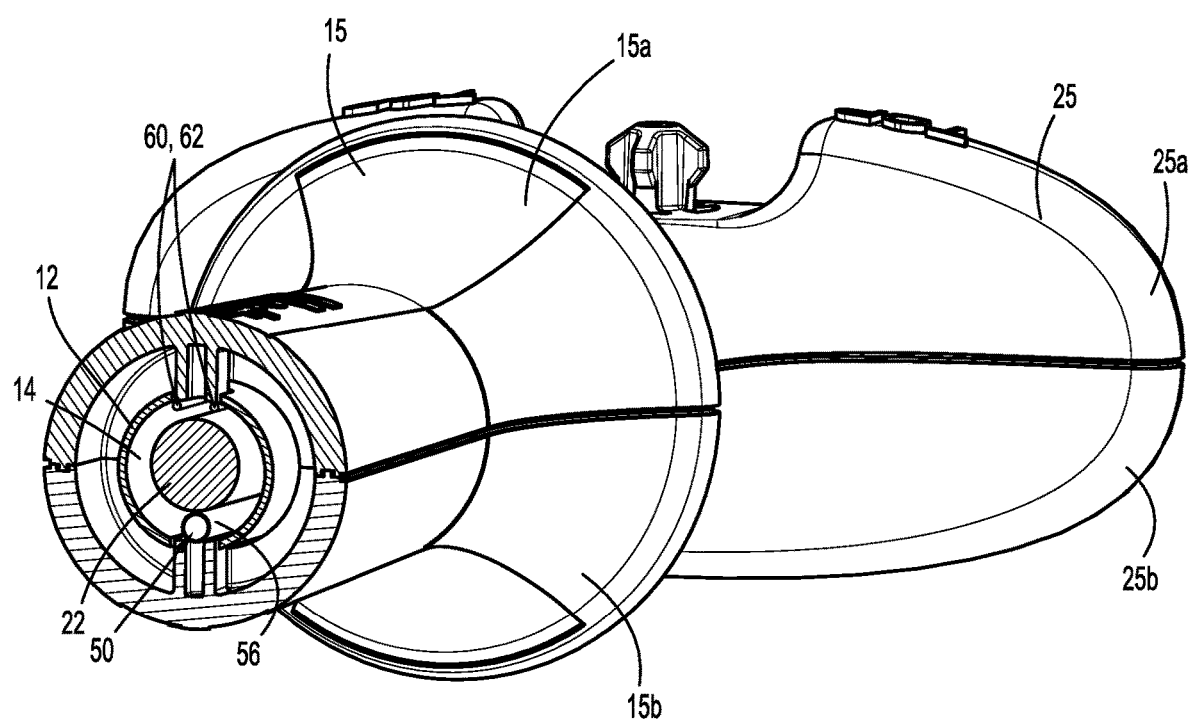
FIG. 5 is a cross-sectional view taken along section line 5-5 of FIG. 4.

FIG. 5 is a cross-sectional view of the specimen retrieval device 10 of the present disclosure showing the inner shaft 22 and drain tube 50 within the longitudinal bore 14 of the tubular body 12 at the distal portion of the hand grip 15. Both the hand grip 15 of the tubular body 12 and actuation handle 25 of the inner shaft 22 are visible. The inner shaft 22 and drain tube 50 are shown to be positioned within the longitudinal bore 14 of the tubular body 12, and the pull strings 60, 62 are shown positioned within the hand grip 15. In addition, the drain tube 50 is shown to be affixed to the inner shaft 22. In embodiments, the drain tube 50 may be affixed to the inner shaft using any means within the purview of those skilled in the art, including adhesives and the like. Alternatively, in some embodiments, the inner shaft 22 of the specimen retrieval device 10 may include a separate channel (not shown) allowing for passage of the drain tube 50 within the tubular body 12 along the inner shaft 22.

In use, the tubular body 12 of the specimen retrieval device 10 can be inserted through an incision (not shown) with the specimen bag 40 furled about the inner shaft 22 and positioned within the tubular body 12 to position the specimen bag 40 in a body cavity adjacent a surgical site. When the tubular body 12 is properly positioned, the clinician can grip the hand grip 15.

The clinician then pushes the actuation handle 25 on the proximal portion 24 of the inner shaft 22 distally in relation to the hand grip 15 and the tubular body 12, so the distal portion 26 of the inner shaft 22, including the specimen bag 40, exits the distal portion 18 of the tubular body 12. Once the specimen bag 40 has exited the tubular body 12, the specimen bag 40 unfurls from about the inner shaft 22 and the resilient fingers 30, 32 return to their non-deformed state (FIG. 1), thereby opening the mouth 42 of the specimen bag 40 to ensure the specimen bag 40 is deployed.

After a tissue specimen has been placed in the specimen bag 40, the drain tube 50 is used to remove any liquids within the specimen bag 40 (FIG. 2), in embodiments before closing the mouth 42 of the specimen bag 40 and removing the specimen bag 40 from the patient's body. Once the fluids have been removed, the pull strings 60, 62 are pulled proximally (not shown) to close the mouth 42 of the specimen bag 40. In some embodiments, a pull ring (not shown) may be affixed to the proximal portion of the pull strings 60, 62 and used to assist in pulling the pull strings 60, 62.

Once the specimen retrieval device of the present disclosure has been removed from the patient's body, any tissue specimen may be removed from the specimen bag 40 for further examination and the specimen bag 40 may be discarded.

Kits of the present disclosure may include both the specimen retrieval device described above, as well as trocars, graspers, vacuum sources (tubes), combinations thereof, and the like. In some embodiments, these additional devices, such as graspers and/or vacuum sources, may be used to break up the tissue specimen in the specimen bag prior to removing the specimen retrieval device from the body cavity. The vacuum source is also suitable to drain fluids from within the specimen bag 40 through the drain tube 50 and out of the specimen bag 40.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A specimen retrieval device, comprising:
    a tubular body defining a longitudinal bore, the tubular body having a proximal portion, a distal portion, and a hand grip supported on the proximal portion of the tubular body;
    an inner shaft having a proximal portion, a distal portion, an actuation handle supported on the proximal portion of the inner shaft, and a support member extending from a distal portion of the inner shaft;
    a specimen bag supported on the support member at the distal portion of the inner shaft, the specimen bag including a body defining an opening; and
    a drain tube defining a longitudinal bore, the drain tube having a proximal portion, a distal portion communicating with the interior of the body of the specimen bag, and pores at the distal portion of the drain tube.

2. The specimen retrieval device of claim 1, wherein the support member includes a pair of resilient fingers which support the specimen bag and open the opening of the specimen bag in a deployed state.

3. The specimen retrieval device of claim 2, wherein the resilient fingers are positioned adjacent the opening of the specimen bag.

4. The specimen retrieval device of claim 1, wherein the specimen bag is furled about the inner shaft in a non-deployed state.

5. The specimen retrieval device of claim 1, further comprising at least one pull string having a proximal portion and a distal portion encompassing the opening of the specimen bag, wherein the proximal portion of the pull string extends proximally from the actuation handle.

6. The specimen retrieval device of claim 5, wherein the at least one pull string includes two pull strings.

7. The specimen retrieval device of claim 5, wherein the proximal portion of each of the two pull strings extends proximally from the actuation handle.

8. The specimen retrieval device of claim 1, wherein the drain tube passes through the longitudinal bore of the tubular body.

9. The specimen retrieval device of claim 8, wherein the proximal portion of the drain tube extends from the proximal portion of the tubular body.

10. A specimen retrieval device, comprising:
    a tubular body defining a longitudinal bore, the tubular body having a proximal portion, a distal portion, and a hand grip supported on the proximal portion of the tubular body;
    an inner shaft having a proximal portion, a distal portion, an actuation handle supported on the proximal portion of the inner shaft, and a support member extending from a distal portion of the inner shaft;
    a specimen bag supported on the support member at the distal portion of the inner shaft, the specimen bag including a body defining an opening;
    at least one pull string having a proximal portion and a distal portion encompassing the opening of the specimen bag, wherein the proximal portion of the pull string extends proximally from the actuation handle; and
    a drain tube defining a longitudinal bore, the drain tube having a proximal portion, a distal portion communicating with the interior of the body of the specimen bag, and pores at the distal portion of the drain tube.

11. The specimen retrieval device of claim 10, wherein the at least one pull string includes two pull strings.

12. The specimen retrieval device of claim 11, wherein the proximal portion of each of the two pull strings extends proximally from the actuation handle.

\* \* \* \* \*